(12) United States Patent
Vedage et al.

(10) Patent No.: US 7,465,833 B2
(45) Date of Patent: Dec. 16, 2008

(54) HYDROGENATION OF AROMATIC AMINES TO ALICYCLIC AMINES USING A LITHIUM ALUMINATE-BASED CATALYST

(75) Inventors: Gamini Ananda Vedage, Bethlehem, PA (US); Hao Ding, Macungie, PA (US); Matthew J. Engel, Emmaus, PA (US); Eugene George Lutz, Lenhartsville, PA (US); Lenore Ann Emig, Westford, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 115 days.

(21) Appl. No.: 11/233,439

(22) Filed: Sep. 22, 2005

(65) Prior Publication Data

US 2007/0066849 A1     Mar. 22, 2007

(51) Int. Cl.
*C07C 209/00* (2006.01)
*C07C 209/02* (2006.01)

(52) U.S. Cl. ...................... 564/450; 564/451
(58) Field of Classification Search .......... 564/451, 564/450
See application file for complete search history.

(56) References Cited

U.S. PATENT DOCUMENTS

| | | | |
|---|---|---|---|
| 2,511,028 A | 6/1950 | Whitman | |
| 2,606,924 A | 8/1952 | Whitman | |
| 2,606,925 A | 8/1952 | Whitman | |
| 2,606,928 A | 8/1952 | Barkdoll et al. | |
| 2,822,392 A * | 2/1958 | Illich, Jr. et al. | 564/450 |
| 3,636,108 A * | 1/1972 | Brake | 564/450 |
| 3,644,522 A | 2/1972 | Brake et al. | |
| 3,697,449 A | 10/1972 | Brake | |
| 3,959,374 A | 5/1976 | Brennan et al. | |
| 4,448,995 A | 5/1984 | Allen | |
| 4,946,998 A | 8/1990 | Casey et al. | |
| 5,023,226 A | 6/1991 | Immel et al. | |
| 5,773,657 A | 6/1998 | Ruetter et al. | |
| 6,184,416 B1 * | 2/2001 | Ding et al. | 564/450 |

FOREIGN PATENT DOCUMENTS

| | | |
|---|---|---|
| DE | 21 32 547 C2 | 11/1982 |
| DE | 38 01 755 A1 | 1/1988 |
| DE | 42 07 314 A1 | 9/1993 |
| EP | 1604972 A1 | 12/2005 |
| EP | 1630155 A1 | 3/2006 |

OTHER PUBLICATIONS

Narayanan, S., et al., "Comparison of Hydrogen Adsorption and Aniline Hydrogenation Over Co-Precipitated Co/$Al_2O_3$ and Ni/$Al_2O_3$ Catalysts," Catalysts Section, Indian Institute of Chemical Technology, Hyderabad—500007, India, *J. Chem. Soc., FaradayTrans.*, vol. 93, pp. 2009-2013 (1997).
Vishwanathan, V., et al., "A Direct Correlation Between Dispersion, Metal Area, and Vapour Phase Hydrogenation of Aniline; a First Report," *J. Chem.Soc., Chem. Commun.*, pp. 78-80 (1990).
Narayanan, S., et al., "Nickel-Alumina Prepared by Constant and Varying pH Method: Evaluation by Hydrogen-Oxygen Chemisorption and Aniline Hydrogenation," *Applied Catalysis A: General*, vol. 129 (1), pp. 9-19 (1995).
Vishwanathan, V., et al., "Gas Phase Aniline Hydrogenation Over Supported Rhodium/Alumina Catalyst," *Indian Journal of Chemistry*, vol. 30A, pp. 679-681 (1991).

* cited by examiner

*Primary Examiner*—Daniel M Sullivan
*Assistant Examiner*—Yate' K Cutliff
(74) *Attorney, Agent, or Firm*—Rosaleen P. Morris-Oskanian

(57) ABSTRACT

The present invention relates to processes for the catalytic hydrogenation of aromatic amines to their acyclic counterparts using a ruthenium catalyst on a lithium aluminate support. The hydrogenation process comprises contacting an aromatic amine with hydrogen in the presence of a ruthenium catalyst under temperature and pressure conditions suitable to effect ring hydrogenation. The process is especially useful for hydrogenating aniline to cyclohexylamine.

24 Claims, No Drawings

HYDROGENATION OF AROMATIC AMINES TO ALICYCLIC AMINES USING A LITHIUM ALUMINATE-BASED CATALYST

FIELD OF THE INVENTION

The present invention provides processes for hydrogenating aromatic compounds in which there is at least one amino functionality bonded to an aromatic nucleus and, more specifically, processes for hydrogenating aromatic amino compounds to the corresponding cycloaliphatic amino compounds. In particular, a process for hydrogenating aromatic amines to alicyclic amines using ruthenium on a lithium aluminate support is disclosed.

DESCRIPTION OF RELATED ART

Supported metal catalysts have been widely used in the petroleum and petrochemical industry for reforming, isomerization, and cracking among other applications. Supported transition-metal catalysts are used in steam reforming, hydrocracking, hydrodesulfurisation, and Fischer-Tropsch (FT) synthesis for the conversion of natural gas into liquid fuels with low sulfur content, low aromaticity, low centane number and good cold flow properties.

Selective hydrogenation reactions using supported transition metal catalysts have also found significant importance commercially in the area of aromatic amine hydrogenation. For example, aniline and methylene dianiline (MDA) hydrogenation is an important process for the industrial production of compounds such as cyclohexylamine (CHA), N-phenylcyclohexylamine (NPCHA), bis(para-aminocyclohexyl)methane (PACM) and dicyclohexylamine (DCHA), all of which are useful as intermediates in a variety of commercial processes, or have specific commercial utility themselves. The conversion and selectivity for such selective hydrogenations, however, have been found to vary depending upon the metal used, and the catalyst system involved. Consequently, numerous attempts to optimize such hydrogenation processes have been made over the years.

There is substantial literature in the art with respect to the hydrogenation of aromatic amines, including aniline and bridged aromatic amines, e.g., aniline hydrogenation to produce cyclohexylamine (CHA), and methylenedianiline (MDA) hydrogenation to produce 4,4'-methylenedi(cyclohexylamine), also referred to as bis(para-aminocyclohexyl)methane (PACM), and bis(4-aminocyclohexyl)methane. The hydrogenated form of bis-aromatic amines typically exist as a mixture of isomers, e.g., the cis, cis-; cis, trans-; and trans, trans-. Often it is desirable to produce a product having a specific isomer content, as the isomer content in the mixture not only influences the physical form of the product but also influences the properties of products in which they are incorporated. For example, in the case of PACM, a low trans, trans-isomer content (20%) in the mixture, commonly referred to as PACM-20, exists as a liquid product while a mixture high in trans, trans-isomer content (50%), commonly referred to as PACM-48, leads to a solid form product. For certain applications, such as the manufacture of polyamide fibers and epoxy additives, it often is beneficial to use PACM-48 instead of PACM-20.

Some of the early hydrogenation work to produce cycloaliphatic amines, such as PACM and cyclohexylamine (CHA) from aniline, is described in U.S. Pat. Nos. 2,511,028; 2,606,924; 2,606,925; and 2,606,928. The processes described in these patents involve the hydrogenation of methylenedianiline (MDA) to bis(para-aminocyclohexyl)methane at pressures in excess of 200 psig, preferably in excess of 1,000 psig, and at temperatures in the range of 80° C. to 275° C. utilizing a ruthenium catalyst. The hydrogenation is carried out under liquid phase conditions and an inert organic solvent is used in the process. Typically, a liquid product having a trans, trans-isomer content of 15-23% is obtained. Ruthenium catalysts utilized for the hydrogenation process include ruthenium oxides such as ruthenium sesquioxide and ruthenium dioxide, as well as ruthenium salts.

U.S. Pat. Nos. 3,696,108 and 3,644,522, disclose processes for manufacturing PACM by hydrogenating methylenedianiline. As described in these patents, it was found that if ruthenium was carried on a support and the support was alkali-moderated, the catalyst was much more active and catalytically effective in producing the desired hydrogenated PACM product. Alkali moderation was effected by contacting the catalyst and support with alkali metal hydroxide or an alkoxide; also, such alkali moderation of the catalyst could be effected prior to hydrogenation or in situ during the hydrogenation. U.S. Pat. No. 3,697,449, describes supported ruthenium catalysts moderated with an alkali metal hydroxide or alkoxide (e.g., NaOH, KOH, or NaOMe) formed by mixing the supported catalyst and the alkali metal compound in the reaction medium of a hydrogenation process. The supported catalyst are described to ruthenium on an inert carrier, such as alumina, barium sulfate, and kieselguhr, and the moderated catalyst reportedly catalyze the hydrogenation of aromatic amines to the corresponding saturated cyclic amines.

U.S. Pat. No. 3,959,374 discloses a process for the preparation of PACM by pretreating a mixed methylenedianiline system with a nickel containing hydrogenation catalyst prior to hydrogenation with ruthenium. The pretreatment was alleged to overcome low yields (52.4%) and long reaction times associated with the use of nickel and cobalt. Ruthenium catalysts, although commonly used for hydrogenation, were reportedly not suited for hydrogenation of a feed containing impurities. e.g., isomeric impurities. These impurities in the feed allegedly caused a rapid decline in activity and hydrogenation efficiency.

Similar transition metal systems have been described in the literature for the selective hydrogenation of aniline to cyclohexylamine using a variety of Group 9 and Group 10 transition metal catalysts on alumina supports. These have included Rh/$Al_2O_3$ catalysts [Vishwanathan, V., et al., *J. Chem. Soc., Chem. Commun.*, pp. 78-80 (1990)], Ni/$Al_2O_3$ catalysts, and Co/$Al_2O_3$ [Narayanan, S., et al., *J. Chem. Soc., Faraday Trans.*, Vol. 93 (10); pp. 2009-2013 (1997)], all of which have varying degrees of selectivity and success, depending upon the catalyst system used. These reports discuss correlations as to the size, metal area, dispersion, etc. of the catalysts used in relation to the degree of selectivity achieved with the various hydrogenation catalyst systems. [Narayanan, S., et al., *Applied Catalysis A: General*, Vol. 129 (1); pp. 9-19 (1995); Vishwanathan, V., et al., *Indian J. Chem. A*, Vol. 30; p. 679 (1991)].

U.S. Pat. No. 4,448,995 discloses a process for the catalytic hydrogenation of di(4-aminophenyl)methane to a liquid di(4-aminocyclohexyl)methane product containing from 15-40 wt. % of the trans, trans-isomer. The process comprises hydrogenating the phenyl compound at a hydrogen pressure of at least 500 psi and a temperature from 100-300° C., using a ruthenium catalyst supported on an inert carrier, such as alumina. The catalyst is described to be moderated with a compound such as nitrates, sulfates, alkali metals, and alkaline earth metals.

U.S. Pat. No. 4,946,998 discloses processes for the hydrogenation of methylenedianiline contaminated with impurities utilizing a mixture of rhodium and ruthenium as the catalyst. A hydrogenated methylenedianiline product having a trans, trans-isomer content of from about 14 to 28% is prepared using the mixed metal catalyst system, although higher trans, trans-content can be achieved through high temperature, long reaction times, and high ruthenium concentration. The presence of rhodium permits lower operating temperatures and reduces the percent trans, trans-isomer in the reaction product.

U.S. Pat. No. 5,773,657 describes the hydrogenation of aniline by ruthenium on low surface area (not >15 m²/g) alumina in the liquid phase, giving a selectivity in the conversion to cyclohexylamine (CHA) of greater than 99%. The catalyst consists essentially of ruthenium and, optionally, at least one metal of subgroup I, VII or VIII of the periodic table such as copper, rhenium, cobalt, or nickel, in an amount from about 0.01 to 30 wt. %.

U.S. Pat. No. 6,184,416 describes a process for the catalytic hydrogenation of aromatic amines to their alicyclic counterparts using a rhodium or rhodium/ruthenium catalyst on a lithium aluminate support. According to the specification, the improvement comprises effecting the hydrogenation utilizing a catalyst comprising rhodium on the lithium aluminate support, wherein the ratio of rhodium to lithium aluminate is from 2 to 8 weight parts per 100 weight parts support.

DE 21 32 547 suggests a process for hydrogenating mononuclear and/or polynuclear aromatic diamines to the corresponding cycloaliphatic amines, wherein the process is carried out in the presence of suspended ruthenium catalysts.

DE 38 01 755 describes a ruthenium-catalyst on chromium- or manganese-treated alumina for use in hydrogenating aromatic amines such as aniline to their acyclic amine counterparts, such as cyclohexylamine and/or dicyclohexylamine. The catalyst can contain, in addition to the ruthenium, palladium or platinum on the Cr- or Mn-treated alumina or aluminum spinel carrier.

DE 42 07 314 discloses a procedure for the manufacture of aliphatic amines from aromatic amines using hydrogenation in the presence of an excess of ammonia and catalysts such as ruthenium, palladium, or platinum on alkali- and/or earth-alkali carriers. According to the specification and the examples, the conversions are performed at temperatures from 120-250° C. and pressures from 0.1-5 bar.

The problem with using many of these previously-described supported catalyst systems in commercial scale hydrogenations of functionalized aromatics, such as aromatic amines, is that these supported catalysts simultaneously catalyze coupling reactions that give undesirable byproducts. Further, while both rhodium and ruthenium have exhibited activity in such hydrogenation reactions, rhodium is preferred due to its higher degrees of activity and selectivity despite its higher cost for use. Thus, there exists a need for a catalyst system which uses the lower-costing ruthenium and simultaneously provides both high activity and high selectivity when used in ring hydrogenation reactions of aromatic amines.

SUMMARY OF THE INVENTION

This invention relates to an improved process for producing cycloaliphatic amines such as cyclohexylamine (CHA) and bis(para-aminocyclohexyl)methane (PACM) by the catalytic hydrogenation of aromatic amines to produce their hydrogenated and thermodynamically stable isomeric counterparts. The present invention provides, in one aspect, a process for catalytically hydrogenating aromatic amines to their ring hydrogenated counterparts, the process comprising the steps of contacting the aromatic amine with hydrogen in the presence of a catalyst on a mixed metal support, wherein the catalyst comprises ruthenium, and the mixed metal support is a lithium aluminate support.

In yet another aspect of the present invention, a process for catalytically hydrogenating aromatic amines of Formula (I) or Formula (II), shown below, is described, and the process comprises contacting the aromatic amine with hydrogen in the presence of a ruthenium catalyst on a mixed metal support, the mixed metal support being a lithium aluminate support.

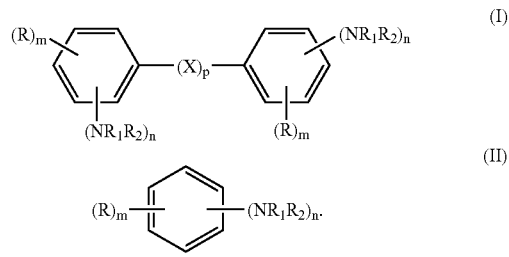

wherein:
R is hydrogen, halogen, linear or branched $C_1$-$C_{12}$ alkyl, linear or branched $C_1$-$C_{12}$ alkoxy, linear or branched $C_1$-$C_{12}$ alkoxyalkyl, or $C_1$-$C_{12}$ alkylamino;
$R_1$ and $R_2$ are independently hydrogen, or linear or branched $C_1$-$C_{12}$ alkyl;
X, when present, is a linear or branched $C_1$-$C_6$ alkylene;
m is 0 or an integer 1-3;
n is 1 or 2; and
p is 0 or 1.

In a further aspect of the present invention, a process for catalytically hydrogenating aniline to cyclohexylamine is provided, wherein the process comprises contacting aniline in a solvent or diluent with hydrogen in the presence of a ruthenium catalyst on a mixed-metal support, the mixed metal support being a lithium aluminate support.

In another aspect, the present invention provides a method of making cyclohexylamine from aniline, the method comprising the steps of contacting aniline in a solvent or diluent with hydrogen in the presence of a ruthenium catalyst on a lithium aluminate support for a period of time sufficient to produce cyclohexylamine, wherein the cyclohexylamine made by such a process, following isolation, can be used in an industrial application or as a chemical intermediate, such as a corrosion inhibitor.

DEFINITIONS

The following definitions are provided in order to aid those skilled in the art in understanding the detailed description of the present invention.

The term "alkyl", alone or in combination, means an acyclic, saturated straight, branched, or cyclic, primary, secondary, or tertiary hydrocarbon, including those containing from 1 to 12 carbon atoms or from 1 to 6 carbon atoms. Said alkyl radicals can be optionally substituted with groups as defined below. Examples of such radicals include methyl, ethyl, chloroethyl, hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The terms "alkoxy" and "alkoxyalkyl" embrace linear or branched oxy-containing radicals each having alkyl portions of from one to about twelve carbon atoms, such as the methoxy or ethoxy radical. The term "alkoxyalkyl" also embraces alkyl radicals having one or more alkoxy radicals attached to the alkyl radical, that is, to form monoalkoxyalkyl and dialkoxyalkyl radicals. Other alkoxy radicals are "lower alkoxy" radicals having one to six carbon atoms. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "Aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "aryl", or "aromatic", as used herein, alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Said "aryl" group may have 1 to 3 substituents termed "heteroaryl" such as heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy.

The terms "halo" and "halogen" mean halogens such as fluorine, chlorine, bromine or iodine atoms.

The term "amino" includes primary, secondary, and tertiary amines. An amino moiety can be represented generally by the formula—$NR_1R_2$, wherein $R_1$ and $R_2$ are independently hydrogen or substituted or unsubstituted alkyl.

The term "substituted", means that one or more hydrogen on the designated atom or substituent is replaced with a selection from the indicated group, provided that the designated atom's normal valency is not exceeded, and that the substitution results in a stable compound.

DETAILED DESCRIPTION OF THE INVENTION

The present invention addresses the need for alternative methods for commercial scale hydrogenations of functionalized aromatics, such as aromatic amines, using metal-supported catalysts that offer high degrees of selectivity in ring hydrogenation while minimizing the catalysis of coupling reactions that result in byproduct formation. The methods provide means whereby aromatic amines can be ring hydrogenated using ruthenium on a lithium aluminate matrix, wherein the reaction proceeds in high overall product formation and low byproduct formation.

While compositions and methods are described in terms of "comprising" various components or steps, the compositions and methods can also "consist essentially of" or "consist of" the various components and steps.

Aromatic Amine Compounds

Aromatic compounds having at least one amino group bonded to it, which can be hydrogenated in accordance with the process of the present invention to give the corresponding cycloaliphatic amino compounds, are aromatic amines of Formula I or Formula II, below,

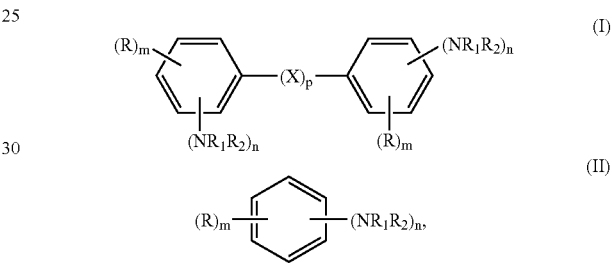

wherein:
R is hydrogen, halogen, linear or branched $C_1$-$C_{12}$ alkyl, linear or branched $C_1$-$C_{12}$ alkoxy, linear or branched $C_1$-$C_{12}$ alkoxyalkyl, or $C_1$-$C_{12}$ alkylamino;
$R_1$ and $R_2$ are independently hydrogen, or linear or branched $C_1$-$C_{12}$ alkyl;
X, when present, is a linear or branched $C_1$-$C_6$ alkylene;
m is 0 or an integer 1-3;
n is 1 or 2; and
p is 0 or 1.

Such aromatic amines include monoamines, diamines, and triamines. Non-limiting examples of aromatic amines of Formula I and/or Formula II suitable for use with the present process include but are not limited to aniline; 2-ethyl aniline; N,N-dimethylaniline; N-ethyl-N-methylaniline; 2,4-diamino-N-phenylaniline; o, m, and p-phenylenediamine; 2,4-diaminotoluene; 1,2,4,5-tetraminobenzene; 2,5-bis(trifluoromethyl)aniline; 4-methoxy-m-phenylenediamine; 2-chloro-4-(trifluoromethyl)aniline; 2-bromo-4-(trifluoromethyl)aniline; 4-amino-m-cresol; 4-amino-2,5-xylenol; 4-amino-N-phenylaniline; 2-amino-N-methylaniline; 2-methoxy-S-methylaniline; o, m, and p-aminobenzonitrile; N-methyl aniline; o, m, and p-toluidine; N-isobutyl-p-phenylenediamine; o, m, and p-xylylenediamine; o, m, and p-anisidine; N-isoamyl-p-phenylenediamine; N-benzyl-p-phenylenediamine; N-cyclohexyl-p-phenylenediamine; N,N'-di (n-propyl)-p-phenylenediamine; N-(n-butyl)-N'-benzyl-p-phenylenediamine; N,N'-dibenzyl-p-phenylenediamine; N-ethyl-m-phenylenediamine; —N-ethyl-o-phenylenediamine; N-methyl-m-phenylenediamine; N,N-diethyl-p-phenylenediamine; N-methyl-N-(n-propyl)-p-phenylenediamine; N-(p-aminophenyl)piperidine; benzylamine; N-isopropylaniline; N-ethyl-o-toluidine; N-ethyl-N-benzyl-m-toluidine; p-(N,N-dimethylamino)benzylamine; N-phenylbenzylamine; N-ethyl-N-phenylbenzylamine; benzidine; o,o'-tolidine; 4,4'-methylenedi(1-naphthylamine); 4,4'-oxydianiline; 4,4'-ethylenedianiline; 4,4'-methylenebis(3-methoxyaniline); 4,4'-methylenedibenzylamine; 4,4'-methylenebis(N-ethyl-o-toluidine); 2,4-bis(4-aminobenzyl)aniline; 4,4'-methylenebis(N,N-dimethylaniline); 4,4'-methylenebis(N-methylaniline); N,N,N',N'-tetramethylbenzidine; bis(3,4-diaminophenyl)methane; bis(3-methyl-4-aminophenyl) methane; and 4,4'-methylene dianiline (MDA). Preferably, and in accordance with one aspect of the invention, the aromatic amine is aniline or methylene dianiline (MDA).

Catalyst

The catalysts used to effect the hydrogenation of an aromatic compound having at least one amino group bonded to it, in accordance with the present invention, is a ruthenium catalyst. The catalysts can be prepared by applying ruthenium to a lithium spinel support, or carrier. The application can be achieved by impregnating, coating, deposition by co-precipitation, or other suitable processes, such as spray deposition. Typically, and in accordance with one aspect of the present invention, the lithium aluminate support is impregnated with ruthenium by contacting the support with an aqueous ruthenium salt solution, e.g., by spraying or co-precipitation using pH adjustment. Such methods are known as incipient wetness techniques. The ruthenium salt solution can be applied to the carrier (or carriers) in an amount such that from about 0.01% to about 30% by weight of ruthenium is present on the carrier(s).

In accordance with the present invention, the catalysts prepared and used in accordance with the present invention contain from about 0.01% by weight to about 30% by weight, based on the total weight of the catalyst, of ruthenium. Those of skill in the art, however, will recognize that this value will be constrained by the available surface on the support. Preferably, the catalyst will contain from about 0.01% to about 20% by weight, and more preferably, from about 0.1% to about 10% by weight, based on the total weight of the catalyst, of ruthenium. Alternatively, the total metal surface area on the catalyst is preferably from about 0.01 $m^2/g$ to about 10 $m^2/g$ of the catalyst, and more preferably from about 0.05 $m^2/g$ to about 8 $m^2/g$ of the catalyst. Suitable ruthenium metal surface areas on the catalyst, in accordance with the present invention, include about 0.01 $m^2/g$, about 0.02 $m^2/g$, about 0.03 $m^2/g$, about 0.04 $m^2/g$, about 0.05 $m^2/g$, about 0.06 $m^2/g$, about 0.07 $m^2/g$, about 0.08 $m^2/g$, about 0.09 $m^2/g$, about 0.1 $m^2/g$, about 0.5 $m^2/g$, about 1 $m^2/g$, about 2 $m^2/g$, about 3 $m^2/g$, about 4 $m^2/g$, about 5 $m^2/g$, about 6 $m^2/g$, about 7 $m^2/g$, about 8 $m^2/g$, about 9 $m^2$ μg, and about 10 $m^2/g$, as well as any range or value between any two of these values, e.g., from about 0.07 $m^2$ μg to about 4 $m^2/g$.

Suitable ruthenium salts for the preparation of the ruthenium salt solutions include but are not limited to the ruthenium carbonates, such as ruthenium carbonate ($Ru(CO_3)_3$); ruthenium carboxylates, such as ruthenium (II, III) μ-oxoacetate [$(CH_3CO_2)_7Ru_3O\cdot 3H_2O$]; ruthenium carbonyls; ruthenium halides, such as ruthenium bromide ($RuBr_3$), ruthenium chloride ($RuCl_3$), ruthenium chloride hydrate ($RuCl_3\cdot xH_2O$), and ruthenium iodide ($RuI_3$); ruthenium nitrates, such as ruthenium nitrate [$Ru(NO_3)_3\cdot xH_2O$]; ruthenium oxides, such as ruthenium oxide ($RuO_2$) and ruthenium (IV) oxide hydrate ($RuO_2\cdot xH_2O$); and ruthenium nitrosylnitrates, such as ruthenium nitrosyl nitrate [$Ru(NO)(NO_3)_x(OH)_y$, wherein x+y=3]; as well as ruthenium chlorine complexes, ruthenium amine complexes, or ruthenium nitrite complexes, as well as combinations of any of the above salts and/or complexes.

Carrier/Support

Lithium spinel ($LiAl_5O_8$), also referred to herein as lithium aluminate, is the preferred support for the catalyst of the present invention. This spinel support is a known composition and is known as a support for some catalytic systems. The $LiAl_5O_8$ support can be made according to the teachings of U.S. Pat. No. 6,184,416. The lithium spinel support is usually made by a solution method wherein an aqueous lithium salt is mixed as a solution with alumina followed by drying and calcination, typically in air. Calcination is typically effected at temperatures in the range from about 500° C. to about 1500° C., preferably from about 700° C. to about 1000° C. to ensure the complete formation of the LiAl5O8 composition. The calcination time typical requires at least 10 hours, and more preferably is carried out for a period of time about 20 to about 25 hours. In formulating the lithium aluminum support, the level of lithium salt is controlled so as to provide an atomic lithium/aluminum ratio of from about 0.2 to about 1.5 to about 5.

The lithium aluminate support can also be made by a solid state reaction between a lithium salt and alumina. As with the solution method, the mixture is dried and then calcined at essentially the same high temperatures over extended periods of time. Lithium salts include LiCl, LiBr, LiF, $Li_2O$, $Li_2SO_4$, $LiNO_3$, LiOH, $Li_2CO_3$, $CH_3COOLi$, and HCOOLi with a preference given to $Li_2CO_3$, $LiNO_3$, $CH_3COOLi$. Sources of alumina include alpha-alumina, chi-alumina, gamma-alumina, eta-alumina, kappa-alumina, delta-alumina, and theta-alumina. For economic reasons and/or considerations, lower cost alumina precursors such as gibbsite ($Al(OH)_3$), boehmite (AlO(OH)), bayerite ($Al(OH)_3$), and diaspore ($HAlO_2$), as well as polymorphs thereof, can also be used.

While those of skill in the art will recognize that the ruthenium/lithium aluminate catalysts used herein will have variations in the surface area ($S_{BET}$), pore volume ($V_p$), pore diameter ($D_p$), and bulk density ($d_B$), the lithium aluminate support materials which can be used for producing the catalysts used in accordance with the present invention are preferably those which are macroporous and have a mean pore diameter of at least about 50 nm, preferably at least about 100 nm, and more preferably at least about 500 nm, and whose surface area measured by the BET method is not more than about 50 $m^2/g$, preferably not more than about 25 $m^2/g$, in particular not more than about 15 $m^2/g$, and most preferably not more than about 10 $m^2/g$. The mean pore diameter of the lithium aluminate support is preferably from about 100 nm to about 200 μm, more preferably from about 500 nm to about 50 μm. The BET surface area of the support is preferably from about 0.2 $m^2/g$ to about 25 $m^2/g$, and more preferably from about 0.5 $m^2$ μg to about 10 $m^2/g$, as well as any value between these ranges, e.g., from about 1 $m^2/g$ to about 5 $m^2/g$, or about 1.3 $m^2/g$.

The surface area of the support (typically measured prior to use), can be determined using any number of methods known to those of skill in the art. Suitable methods include the BET (Brunauer, Emmett, & Teller) method using $N_2$ adsorption, such as described in DIN (Deutsches Institut für Normung, e.V.) Standard 66131. The determination of the mean pore diameter and the pore size distribution can be carried out by Hg porosimetry, in particular in accordance with DIN 66133.

A ruthenium salt is combined with the lithium aluminate support, based upon its weight as metal, in an amount sufficient to provide a ratio of about 0.1 to about 25 weight parts ruthenium per 100 weight parts of support. Preferably, the level of ruthenium is from about 2 to about 8 weight parts ruthenium per 100 weight parts of support. Ruthenium is added to the support by either the incipient wetness (IW) impregnation method or co-precipitation in the presence of a base in water. Preferred bases for use with the present invention include LiOH, $Li_2CO_3$, or $Na_2CO_3$. The catalyst comprised of ruthenium and the lithium aluminate support is dried and heated to a temperature of <400° C.

Hydrogenation

The hydrogenation process, in accordance with the present invention, is carried out at pressures and temperatures sufficient to effect the desired transformation. Preferably, the presently described processes are effected at pressures between about 50 psi and about 4,000 psi, more preferably at a pressure between about 50 psi and about 2,000 psi, and still more preferably at a pressure between about 50 psi and about 1,000 psi, over the period of time necessary to effect the desired transformation. Specific hydrogenation pressures suitable for use in carrying out the processes of the present invention include pressure of about 50 psi, about 100 psi, about 150 psi, about 200 psi, about 250 psi, about 300 psi, about 350 psi, about 400 psi, about 450 psi, about 500 psi, about 550 psi, about 600 psi, about 650 psi, about 700 psi, about 750 psi, about 800 psi, about 850 psi, about 900 psi, about 950 psi, and about 1000 psi, as well as any pressure range between any two of these pressures, e.g., from about 200 psi to about 850 psi. Preferred temperatures for the described process are from about 50° C. to about 300° C., and more preferably from about 100° C. to about 230° C. Specific reaction temperatures suitable for use with the process described herein include temperatures of about 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 205° C., 210° C., 215° C., 220° C., 225° C., and 230° C., as well as any temperature range between any two of these temperatures, e.g., from about 130° C. to about 210° C.

The hydrogenation process can be carried out either continuously or batchwise. In continuous processes, the amount of aromatic compound (or compounds) intended for the hydrogenation can be from about 0.05:3, and more typically from about 0.1:1.0, per 1 liter of catalyst, per hour.

The hydrogenation gases which can be used, in accordance with the process of the present invention, can be any of numerous desired gases which contain free hydrogen and do not contain any detrimental amounts of compounds which can potentially act as catalyst poisons, such as CO. Preferably, the hydrogenation gas is pure hydrogen, although reformer waste gasses can also be used if they are poison free.

The hydrogenation process of the present invention can be generally described as shown in Scheme 1 below, illustrated for the case of the selective ring hydrogenation of aniline (A) to cyclohexylamine (CHA). According to the process, aniline, preferably in an appropriate, inert solvent, is contacted with hydrogen gas ($H_2$) in the presence of a ruthenium metal catalyst on a lithium aluminate support, at a temperature from about 50° C. to about 300° C., and a hydrogenation pressure from about 50 psig to about 2,000 psig, for a period of time sufficient to obtain the desired product, as analyzed by gas chromatography (GC). In accordance with the present invention, the ring hydrogenation product will preferably have a minimal (less than about 5%) amount of residual aromatics and/or byproducts due to unwanted coupling reaction products.

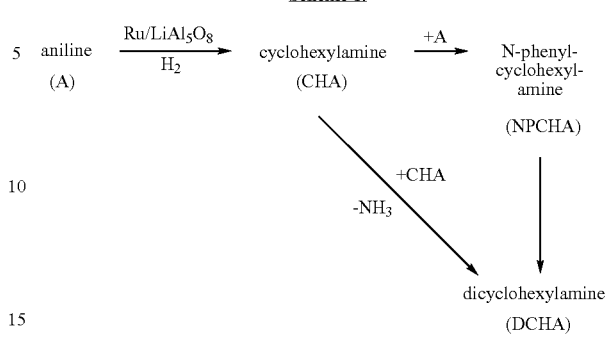

Solvents

As with conventional processes the hydrogenation of aromatic amines using the present ruthenium catalysts carried on a lithium aluminate support is carried out under liquid phase conditions. Liquid phase conditions are maintained typically by carrying out the hydrogenation in the presence of a solvent. Although it is possible to effect reaction in the absence of a solvent, the processing is usually much simpler when a solvent is employed. Generally speaking, any number of known, suitable solvents useful in hydrogenation reactions can be used for the presently described hydrogenation processes, as long as there is no active hydrogen in the solvent used. In accordance with the present invention, representative solvents suited for effecting the hydrogenation of aromatic amines in the presence of ruthenium metal carried on a lithium aluminate support include saturated aliphatic and alicyclic hydrocarbons such as cyclohexane, hexane, heptane, pentane, and cyclooctane; low molecular weight alcohols, such as methanol, ethanol, and isopropanol; and aliphatic and alicyclic hydrocarbon ethers, including n-propyl ether, isopropyl ether, n-butyl ether, methyl tert-butyl ether (MTBE), amyl ether, diethyl ether ($Et_2O$), tetrahydrofuran (THF), dioxane, and dicyclohexyl ether. Alicyclic, as used herein, means those members of the class of non-aromatic organic, ring compounds containing carbon and hydrogen, such as THF and dioxane. Hydrocarbon ethers, such as tetrahydrofuran, are preferred for use as a solvent in accordance with the present disclosure. In accordance with the present invention, the solvent or diluent can also contain small amounts (e.g., <1 wt. %) of water.

Although in some processes water can be present in the organic solvent, or used as a co-solvent, it is preferred that the system be maintained with less than 0.5% by weight water. Water, when present in the system, tends to increase the amount of by-product alcohols and heavy condensation products during the hydrogenation process. Also, there is a tendency to deactivate the catalyst system in part by dissolving the support phase. An advantage of the lithium aluminate supported catalyst of the present invention is that it tolerates the presence of water better than other supported catalysts, even when water content is up to 0.5% by weight.

When a solvent is used, it can be used in concentrations as low as 50% by weight based upon the aromatic amine introduced into the reaction and typically the solvent is used at levels from about 75 to about 200% by weight of the starting compound. Under some circumstances solvent amount as high as 1000 to 2000% based upon the weight of aromatic amine are used.

Products

The products of the selective ring hydrogenation or aromatic amines prepared according to the processes of the present invention can be used in a number of commercial applications, and as intermediates in a variety of chemical products. For example, cyclohexylamine (CHA), prepared by the hydrogenation of aniline using a ruthenium/lithium aluminate catalyst in accordance with the present disclosure can be used as a corrosion inhibitor, in the manufacture of corrosion inhibitors, as boiler water treatments, and in oil field production applications. Similarly, cyclohexylamine prepared according to the process described herein can be used as a chemical intermediate in the manufacture of insecticides, pesticides, cyclamate sweeteners, plasticizers, dry-cleaning soaps, rubbers, elastomers, dyes, or gas absorbents, among other products.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Examples 1-5 illustrate the preparation of the lithium aluminate support according to the teachings in U.S. Pat. No. 6,184,416.

Example 1

Preparation of Lithium Aluminate ($LiAl_5O_8$) from Lithium Acetate

Lithium acetate ($CH_3COOLi.2H_2O$, 40.0 g) was added to Gibbsite (C31 alumina 153 g) in a plastic container and mixed. The mixture was then transferred to a ceramic dish and dried at 110° C. for 24 h and calcined at 1000° C. in air for 20 h (ramp: 5° C./min). (Ramp refers to increasing the temperature from room temperature to the final temperature at a specified rate per minute.) Yield: ~100 g of white powder (powder x-ray diffraction (XRD) indicated $LiAl_5O_8$ with a purity over 98%).

Example 2

Preparation of Lithium Aluminate ($LiAl_5O_8$) from Lithium Carbonate

Lithium carbonate ($Li_2CO_3$, 14.5 g) was added to Gibbsite (C31 alumina from Alcoa, 153 g) in a plastic container and mixed well. The mixture is then transferred to a ceramic dish and calcined at 1000° C. in air for 24 h (ramp: 5° C./min). Yield: ~100 g of white powder (XRD indicated $LiAl_5O_8$ with a purity over 98%.)

The above example exhibits synthesizing $LiAl_5O_8$ by solid state reaction between a lithium salt and aluminum hydroxide with the elimination of the use of any solvents. This method is especially suitable for large scale synthesis.

Example 3

Preparation of Lithium Aluminate ($LiAl_5O_8$) from Lithium Hydroxide

Lithium hydroxide ($LiOH.H_2O$, 8.25 g) was added to Gibbsite (C31 alumina, 76.6 g) in 40 ml D.I. (deionized) water. The free-flow suspension was heated on a hot plate with stirring for 30 min to remove water. The resulting solid cake was broken into small pieces and dried in a oven at 110° C. for 16 h. The solid was then ground and calcined at 600° C. (ramp: 5° C./min) for 20 h. Yield: 53 g white powder.

Example 4

Hot Water Wash of $LiAl_5O_8$ $LiAl_5O_8$ (5.0 g) from Example 1 was added to 100 ml of deionized (D.I.) water. The suspension was heated at 85° C. on a hot plate with stirring for 2 h. The remaining solid was collected by filtration and dried at 110° C. for 10 h, at which time 4.8 g of $LiAl_5O_8$ (identified by x-ray diffraction (XRD)) was recovered (96% recovery).

Example 5

Hot Water Wash of $LiAl_5O_8$ from Examples 1-3

5.0 g of $LiAl_5O_8$ from Example 3 was added to 100 ml of d.i. water. The suspension was heated at 85° C. on a hot plate with stirring for 2 h. The remaining solid was collected by filtration and dried at 110° C. for 10 h. Using this approach, 3.4 g material was recovered (68% recovery).

The results show that the sample of $LiAl_5O_8$ calcined at 1000° C. (Examples 1 and 2) was much more water resistant than the $LiAl_5O_8$ supported catalyst combined at a calcination temperature of 600° C. (Example 3). This is evidenced by the two water wash studies. Recovery of the solid after a hot water wash of $LiAl_5O_8$ calcined at 1000° C. was 96%, compared to a recovery of 68% when it was calcined at 600° C.

Example 6

Hydrogenation of Aniline to Cyclohexylamine

The lithium aluminate ($LiAl_5O_8$) support was synthesized as detailed in the above examples. Ruthenium catalyst was prepared by incipient wetness techniques. Aniline (99%) was purchased from Aldrich Chemical Co. (St. Louis, Mo.).

Aniline hydrogenation reactions were carried out using either lithium aluminate-based or carbon-based ruthenium catalysts under a hydrogen pressure of 850 psig. No catalyst reduction was done prior to the hydrogenation. The reaction was run neat with aniline (500 g) in a 1 L stainless steel Parr reactor equipped with mechanical agitator, temperature control and a 0.5µ internal filter for catalyst/product separation. Ruthenium/lithium aluminate (9 g) was used as catalyst. Reaction temperature was 150° C. LiOH modification was done in-situ with 0.4 g $LiOH.H_2O$ in 3.6 g water. Following the pre-set reaction time, the reactor was cooled to room temperature and the products analyzed using gas chromatography. The results are shown in Table I, below. As is apparent, hydrogenation using a catalyst loading of 5% ruthenium on lithium aluminate for a reaction time of about 120 minutes or less (runs 3-5), provided greater than 99% conversion of the aniline to cyclohexylamine, with a minimal (less than about 1%) amount of side-product formation. In comparison, the use of 5% ruthenium on carbon (runs 6-8) produced noticeably less cyclohexylamine and higher (greater than about 1%) amounts of undesired side products.

The use of lithium hydroxide (LiOH) as a favorable additive in such hydrogenation transformations is well established in the literature. As shown in runs 2 and 7 of Table I, however, when the same amount of LiOH was added to both the lithium aluminate-based and the carbon-based catalyst system, the degree of impact on the reaction remains less than that achieved with the use of the aluminate-based catalyst alone for an optimized reaction time. In the case of the carbon-based catalyst (run 7), the addition of the LiOH had only a moderate influence on product formation.

TABLE I

Hydrogenation of aniline using ruthenium on catalyst.

| Run | Catalyst | Reaction time (min) | CHA[1] (%) | DCHA[2] (%) | LiOH added (g) |
|---|---|---|---|---|---|
| 1 | 5% Ru/LiAl$_5$O$_8$ | 180 | 89.2 | 3.3 | — |
| 2 | 5% Ru/LiAl$_5$O$_8$ | 125 | 97.1 | 1.0 | 0.4 |
| 3 | 5% Ru/LiAl$_5$O$_8$ | 120 | 99.6 | 0.22 | — |
| 4 | 5% Ru/LiAl$_5$O$_8$ | 77 | 99.6 | 0.10 | — |
| 5 | 5% Ru/LiAl$_5$O$_8$ | 90 | 99.9 | 0.08 | — |
| 6 | 5% Ru/C | 166 | 86.2 | 10.9 | — |
| 7 | 5% Ru/C | 73 | 91.8 | 5.73 | 0.4 |
| 8 | 5% Ru/C | 85 | 94.1 | 4.81 | — |

[1]CHA = cyclohexylamine.
[2]DCHA = dicyclohexylamine: Products were analyzed by area percent GC using an HP5 column, 25 m long with a 0.17 micron film thickness.

Example 7

Hydrogenation of Methylene Dianiline (MDA) to PACM

The lithium aluminate (LiAl$_5$O$_8$) support was synthesized as detailed in the above examples. Ruthenium catalyst was prepared by incipient wetness. The methylene dianiline (MDA) starting material (98%) was purchased from Aldrich Chemical Co.

MDA hydrogenation reactions were carried out using either lithium aluminate- or alumina (γ-Al$_2$O$_3$)-based ruthenium catalysts under 800 psig of hydrogen pressure. The hydrogenation reactions were carried out in a standard 1 L Parr reactor equipped with a 0.5μ internal filter for catalyst/product separation. 5% Ruthenium on lithium aluminate (5 g) was charged into the reactor with 200 g of tetrahydrofuran (THF), and the mixture was reduced under 850 psi H$_2$ at 190° C. for 4 hours, stirring at 1,000 rpm. The THF was filtered out, and 400 g of 50% MDA in THF was introduced to the reactor. The MDA was then hydrogenated with stirring (1,500 rpm) at 180° C. and 800 psi hydrogen pressure for 8 hours. After cooling the reactor to room temperature, the products were filtered and the reactor re-charged with MDA/THF for additional use. Prior to the second use of the reactor, 5 g of a 15% solution (aq.) of lithium hydroxide monohydrate was added in order to investigate the impact of base upon the transformation. The products analyzed by gas chromatography (GC) using an HP5 column, 25 m long with a 0.17 micron film thickness. The comparative results are shown in Table II.

TABLE II

Results from MDA Hydrogenation.

| Run | Catalyst | Reaction time (min) | Conversion (%) | PACM 2° amines (%) | LiOH added (g) |
|---|---|---|---|---|---|
| 1 | 5% Ru/LiAl$_5$O$_8$ | 480 | 97 | 42.0 | — |
| 2 | 5% Ru/LiAl$_5$O$_8$ | 480 | 96 | 8.8 | 0.75 |
| 3 | 5% Ru/LiAl$_5$O$_8$ | 480 | 77 | 3.0 | — |
| 4 | 5% Ru/LiAl$_5$O$_8$ | 480 | 68 | 1.4 | — |
| 5 | 5% Ru/LiAl$_5$O$_8$ | 480 | 61 | 0.7 | — |
| 6 | 5% Ru/γ-Al$_2$O$_3$ | 480 | 100 | 36.8 | — |
| 7 | 5% Ru/γ-Al$_2$O$_3$ | 480 | 100 | 20.1 | 0.75 |
| 8 | 5% Ru/γ-Al$_2$O$_3$ | 480 | 96 | 34.7 | — |
| 9 | 5% Ru/γ-Al$_2$O$_3$ | 480 | 80 | 32.0 | — |

It is well established in the technical literature that the addition of a base, such as lithium hydroxide (LiOH), can suppress the formation of PACM (para-aminocyclohexylmethane) secondary amine during hydrogenation, the major byproduct resulting from the coupling of PACM. Runs 2 and 7 in Table II demonstrate the effect of lithium hydroxide (LiOH) addition on the reaction. As is evident, the same amount of LiOH added to the aluminate- and the alumina-based ruthenium catalyst demonstrated drastically different degrees of impact. For example, the addition of the LiOH to the ruthenium/lithium aluminate catalyst caused a reduction in secondary amine formation from 42% to 8.8% and a continued decrease in subsequent uses. However, in the case of the ruthenium/alumina catalyst, the secondary amines level decreased only modestly (from 36.8% to 20.1%), and then increased to over 30% in subsequent uses.

Example 8

General Conditions—Hydrogenation of Aniline to Cyclohexylamine

The reaction temperature is between 50-200° C., preferably between 120-170° C. The reaction pressure is between 400 and 4000 psig hydrogen, preferably between 700 and 950 psig. The reaction times may vary from one hour to several days. The ruthenium to aniline ratio ranges from 1:10 to 1:3000, preferably from about 1:1000 to about 1:2000. The basic alkali is added in an amount to provide from 0.1 to 15% by weight of a basic metal compound calculated as alkali metal.

Example 9

General Conditions—Hydrogenation of MDA to PACM

The reaction temperature range is between 130-210° C., preferably from between 170-200° C. The reaction pressure is between 500 and 4000 psig hydrogen, preferably between 600 and 1000 psig. The reaction time varies from one hour to several days. The ruthenium to methylene bridged polyphenylamines ratio ranges form 1:10 to 1:3,000, preferably from about 1:10 to about 1:2000. The basic alkali is added in an amount to provide from about 0.1 to about 15% by weight of a basic metal compound calculated as alkali metal.

We claim:

1. A process for catalytically hydrogenating aromatic amines to their ring hydrogenated counterparts, the process comprising:

contacting the aromatic amine with hydrogen in the presence of a catalyst consisting of ruthenium on a lithium aluminate support, wherein the ratio of ruthenium to lithium aluminate support is from about 2 to about 8 weight parts ruthenium per 100 weight parts support.

2. The process of claim 1, wherein the aromatic amine is selected from the group consisting of compounds of Formula I,

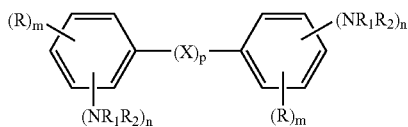

wherein:
R is hydrogen, halogen, linear or branched $C_1$-$C_{12}$ alkyl, linear or branched $C_1$-$C_{12}$ alkoxy, linear or branched $C_1$-$C_{12}$ alkoxyalkyl, or $C_1$-$C_{12}$ alkylamino;
$R_1$ and $R_2$ independently are a hydrogen or linear or branched $C_1$-$C_{12}$ alkyl;
X is linear or branched $C_1$-$C_6$ alkylene;
m is 0, 1, 2, or 3;
n is 1 or 2; and
p is 0 or 1.

3. The process of claim 1, wherein the aromatic amine is selected from the group consisting of compounds of Formula II,

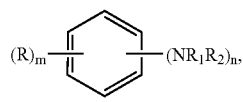

wherein:
R is hydrogen, halogen, linear or branched $C_1$-$C_{12}$ alkyl, linear or branched $C_1$-$C_{12}$ alkoxy, linear or branched $C_1$-$C_{12}$ alkoxyalkyl, or $C_1$-$C_{12}$ alkylamino;
$R_1$ and $R_2$ independently are a hydrogen or linear or branched $C_1$-$C_{12}$ alkyl;
m is 0, 1, 2, or 3; and
n is 1 or 2.

4. The process of claim 1 wherein the aromatic amine is aniline.

5. The process of claim 1 wherein the aromatic amine is methylene dianiline.

6. The process of claim 1 wherein the hydrogenation is carried out in the presence of a solvent or diluent.

7. The process of claim 6 wherein the solvent or diluent is selected from the group consisting of aliphatic and alicyclic hydrocarbons, aliphatic and alicyclic ethers, alcohols, water, and mixtures thereof.

8. The process of claim 6 wherein the solvent or diluent is substantially tetrahydrofuran.

9. The process of claim 1 wherein the hydrogenation pressure is from about 50 psig to about 4000 psig.

10. The process of claim 1, wherein the process is carried out at a temperature from about 50° C. to about 300° C.

11. A process of claim 1, wherein the process is carried out continuously or batchwise.

12. A process for catalytically hydrogenating aromatic amines of Formula I or Formula II,

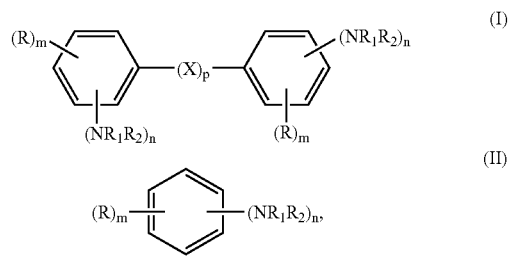

wherein:
R is hydrogen, halogen, linear or branched $C_1$-$C_{12}$ alkyl, linear or branched $C_1$-$C_{12}$ alkoxy, linear or branched $C_1$-$C_{12}$ alkoxyalkyl, or $C_1$-$C_{12}$ alkylamino;
$R_1$ and $R_2$ independently are a hydrogen or linear or branched $C_1$-$C_{12}$ alkyl;
X is linear or branched $C_1$-$C_6$ alkylene;
m is 0, 1, 2, or 3;
n is 1 or 2; and
p is 0 or 1,
the process comprising:
contacting the aromatic amine with hydrogen in the presence of a catalyst consisting of ruthenium on a lithium aluminate support, wherein the ratio of ruthenium to lithium aluminate support is from about 2 to about 8 weight parts ruthenium per 100 weight parts support.

13. The process of claim 12 wherein the aromatic amine is aniline.

14. The process of claim 12 wherein the aromatic amine is methylene dianiline.

15. The process of claim 12 wherein the hydrogenation is carried out in the presence of a solvent or diluent.

16. The process of claim 15 wherein the solvent or diluent is selected from the group consisting of aliphatic and alicyclic hydrocarbons, aliphatic and alicyclic ethers, alcohols, water, and mixtures thereof.

17. The process of claim 15 wherein the solvent or diluent is substantially tetrahydrofuran.

18. The process of claim 12 wherein the hydrogenation pressure is from about 50 psig to about 4000 psig.

19. The process of claim 12 wherein the process is carried out at a temperature from about 50° C. to about 300° C.

20. A process of claim 12 wherein the process is carried out continuously or batchwise.

21. A process for catalytically hydrogenating aniline to cyclohexylamine, the process comprising:
contacting aniline in a solvent or diluent with hydrogen in the presence of a catalyst consisting of ruthenium on a lithium aluminate support, wherein the ratio of ruthenium to lithium aluminate support is from about 2 to about 8 weight parts ruthenium per 100 weight parts support.

22. The process of claim 21 wherein the solvent or diluent is tetrahydrofuran.

23. The process of claim 21 wherein the hydrogenation is carried out at a pressure of from about 200 psig to about 1500 psig and at a temperature of from about 50° C. to about 300° C.

24. The process of claim 1, wherein the ruthenium is from about 0.1% to about 10% of the total weight of the catalyst.

* * * * *